(12) United States Patent
Valaie et al.

(10) Patent No.: US 8,893,883 B2
(45) Date of Patent: *Nov. 25, 2014

(54) MEDICAL DEVICE PACKAGING

(71) Applicant: Cook Medical Technologies LLC, Bloomington, IN (US)

(72) Inventors: Arman H. Valaie, Bloomington, IN (US); Matthew J. Palmreuter, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/717,296

(22) Filed: Dec. 17, 2012

(65) Prior Publication Data

US 2013/0104501 A1    May 2, 2013

Related U.S. Application Data

(63) Continuation of application No. 13/151,664, filed on Jun. 2, 2011, now Pat. No. 8,365,910.

(51) Int. Cl.
| | |
|---|---|
| *B65D 85/00* | (2006.01) |
| *B65D 81/18* | (2006.01) |
| *A61L 2/26* | (2006.01) |
| *B65B 55/02* | (2006.01) |
| *B65D 43/02* | (2006.01) |
| *B65D 51/18* | (2006.01) |
| *A61B 19/02* | (2006.01) |

(52) U.S. Cl.
CPC . *B65D 81/18* (2013.01); *A61L 2/26* (2013.01); *A61B 19/0271* (2013.01); *A61B 19/026* (2013.01); *B65B 55/02* (2013.01); *B65D 43/0202* (2013.01); *B65D 2251/0093* (2013.01); *A61L 2202/182* (2013.01); *A61B 2019/0219* (2013.01); *B65D 2251/0031* (2013.01); *B65D 51/185* (2013.01)
USPC .......................................................... 206/363

(58) Field of Classification Search
CPC ................. B65D 81/18; B65D 51/185; B65D 2251/0031; B65D 43/0202; B65B 55/02
USPC .......................... 206/363, 364, 438, 538, 532; 220/254.7, 254.2
See application file for complete search history.

(56) References Cited

U.S. PATENT DOCUMENTS

| | | |
|---|---|---|
| 3,344,974 A | 10/1967 | Bostrom |
| 3,552,634 A | 1/1971 | Ollier et al. |
| 3,630,346 A | 12/1971 | Burnside |
| 3,835,995 A | 9/1974 | Haines |

(Continued)

*Primary Examiner* — Steven A. Reynolds
*Assistant Examiner* — King M Chu
(74) *Attorney, Agent, or Firm* — Brinks Gilson & Lione

(57) ABSTRACT

A package for containing a medical device can have a bottom portion and inner and outer lids releasably sealed to the bottom portion. The bottom portion defines a cavity for receiving a medical device. A flange extends outward from sidewalls of the bottom portion and includes an inner flange portion and an outer flange portion. The inner flange portion can be recessed below the outer flange portion. The sealed inner lid permits sterilization of the cavity. The outer lid provides a moisture-resistant barrier to the package. A corner portion of the outer lid can extend past a corner of the bottom portion. Upon application of a withdrawing force sufficient to break the seals, the inner lid and the outer lid are together capable of being peeled from the bottom portion.

19 Claims, 13 Drawing Sheets

(56) References Cited

U.S. PATENT DOCUMENTS

| | | | |
|---|---|---|---|
| 4,346,833 A | 8/1982 | Bernhardt | |
| 4,482,053 A | 11/1984 | Alpern et al. | |
| 4,511,035 A | 4/1985 | Alpern et al. | |
| 4,697,703 A | 10/1987 | Will | |
| 4,939,332 A | 7/1990 | Hahn | |
| 4,946,038 A | 8/1990 | Eaton | |
| 5,125,529 A | 6/1992 | Torterotot | |
| 5,165,947 A * | 11/1992 | Colucci et al. | 426/124 |
| 5,447,736 A | 9/1995 | Gorlich | |
| 5,590,778 A | 1/1997 | Dutchik | |
| 5,720,391 A | 2/1998 | Dohm et al. | |
| 5,727,687 A | 3/1998 | Renner | |
| 5,830,547 A | 11/1998 | MacKenzie et al. | |
| 5,868,253 A | 2/1999 | Krueger et al. | |
| 5,916,614 A | 6/1999 | Gorlich | |
| 6,073,767 A | 6/2000 | Cohen et al. | |
| 6,622,864 B1 | 9/2003 | Debbs et al. | |
| 6,648,140 B2 | 11/2003 | Petricca | |
| 6,889,839 B1 * | 5/2005 | Rosten et al. | 206/583 |
| 7,000,770 B2 | 2/2006 | Clarke et al. | |
| 7,316,318 B1 | 1/2008 | Rosten et al. | |
| 7,631,757 B2 | 12/2009 | Petricca | |
| 7,648,030 B2 | 1/2010 | Landis | |
| 7,762,044 B2 | 7/2010 | Clarke et al. | |
| 7,766,164 B2 | 8/2010 | Hurst | |
| 8,365,910 B2 | 2/2013 | Valaie et al. | |
| 2006/0016897 A1 | 1/2006 | Yasuda et al. | |
| 2006/0260967 A1 | 11/2006 | Clarke et al. | |
| 2008/0118609 A1 | 5/2008 | Harlfinger | |
| 2008/0160143 A1 | 7/2008 | Edwards et al. | |
| 2011/0036736 A1 | 2/2011 | Knowlton et al. | |

* cited by examiner

MEDICAL DEVICE PACKAGING

CROSS-REFERENCE TO RELATED APPLICATION

This application is a continuation of U.S. patent application Ser. No. 13/151,664, filed Jun. 2, 2011, which is incorporated herein by reference in its entirety.

TECHNICAL FIELD

The present disclosure relates to packages for storing and transporting sterile items, and more particularly, relates to a tray package for storing medical devices in a moisture-resistant, sterile environment.

BACKGROUND

Drug coated medical devices are typically stored and transported into packages that provide a sterile, bacteria free environment. The package must also be able to maintain the integrity of the drug coating for an effective dosage, usually for a shelf life of one year. Accordingly, certain drug coatings require regulated conditions for efficacy, including moisture, as well as ventilation, light exposure, and oxygen.

Such package typically includes a thermoformed tray containing a drug coated medical device, which is enclosed and sealed within an outer foil pouch. The thermoformed tray may have a TYVEK® material lid to allow the medical devices to be sterilized before being enclosed within the outer foil pouch. Alternatively, the thermoformed tray, without a TYVEK® material lid, is inserted within the outer foil pouch that includes a TYVEK® strip to allow the medical devices to be sterilized after being enclosed within the outer foil pouch. However, the outer foil pouch prevents the end user from viewing the medical device contained therein. In addition, as the packages become larger due to the size of the medical devices, the outer foil package also becomes larger, e.g., 24 inches wide. Such larger foil packages are more susceptible to being compromised, thereby resulting in the possibility of unacceptable levels of bacteria, moisture, ventilation, light exposure, and oxygen. One reason is the increased risk of incomplete sealing and channels, which are formed from folds of the pouches during the sealing process. Another reason is the increased risk of punctured openings in the outer foil package as a result of damage during shipping and handling of the package.

Thus, what is needed is a package specifically configured for drug coated medical devices, which can permit an end user to view the medical devices inside of the package without opening the package. In particular, what is needed is a package configured for moisture-sensitive devices, such as drug coated medical devices, to extend the shelf life of such devices, thereby reducing the costs of scrapping such packages with the medical devices and reducing the costs of environmental wastes.

BRIEF SUMMARY

In one embodiment, a package for containing one or more medical devices, such as drug coated medical devices, is provided. The package can include a bottom portion and an inner and outer lid portions. The bottom portion can include sidewalls and a bottom wall to define a cavity to receive a medical device. A flange can extend outward from top edges of the sidewalls, and include an inner flange portion and an outer flange portion. The inner flange portion may be recessed with respect to the outer flange portion. The inner lid can be releasably sealed to the inner flange portion at a first sealed region. The inner lid can include a sterilizable material to allow the medical device to be sterilized when the inner lid is sealed to the bottom portion. The inner lid and the bottom portion form a microbial-resistant, sterile enclosure for the medical device. The outer lid can overlie the inner lid and be releasably sealed to at least the outer flange portion at a second sealed region. The outer lid can have an environmental member that includes a moisture-resistant material. The outer lid when sealed can maintain a moisture content within the enclosure for the medical device at a desirable level. The outer lid may include a metal foil layer and a desiccant layer, where the metal foil layer arranged to capture the desiccant layer between the inner lid and the metal foil layer.

In one example, a corner portion of the outer lid may extend past a corner of the flange of the bottom portion. Upon application of a withdrawing force to the corner portion of the outer lid sufficient to break at least one of the first and second sealed regions, the inner lid and the outer lid are capable of being peeled together from the bottom portion. In one aspect, a corner portion of the inner lid can have a protruding portion to form a first tab, and the corner portion of the outer lid can overlie the first tab. In another aspect, a corner portion of the inner lid can have a protruding portion that has a folded configuration. In the folded configuration, the protruding portion can extend inward toward the cavity such that a segment of the protruding portion can engage with a lower surface of the outer lid In another embodiment, a method of packaging a medical device is provided, and can include one or more of the following steps. For instance, a medical device can be inserted within a cavity of a bottom portion. The bottom portion can include walls to define the cavity, and a flange extending outward from top edges of the walls. The flange can include an inner flange portion and an outer flange portion. An inner lid can be sealed to the inner flange portion. The inner lid can include a sterilizable material. The inner lid and the bottom portion form a sealed enclosure for the medical device. The sealed enclosure with the medical device can be sterilized so that sealed enclosure is a microbial-resistant, sterile enclosure for the medical device. An outer lid can be sealed to the outer flange portion. The outer lid can overlie the inner lid. The outer lid can have an environmental member including a moisture-resistant material, so that the sealed enclosure is further a moisture-resistant enclosure for the medical device.

DETAILED DESCRIPTION OF THE DRAWINGS AND THE PRESENTLY PREFERRED EMBODIMENTS

Figure 1:
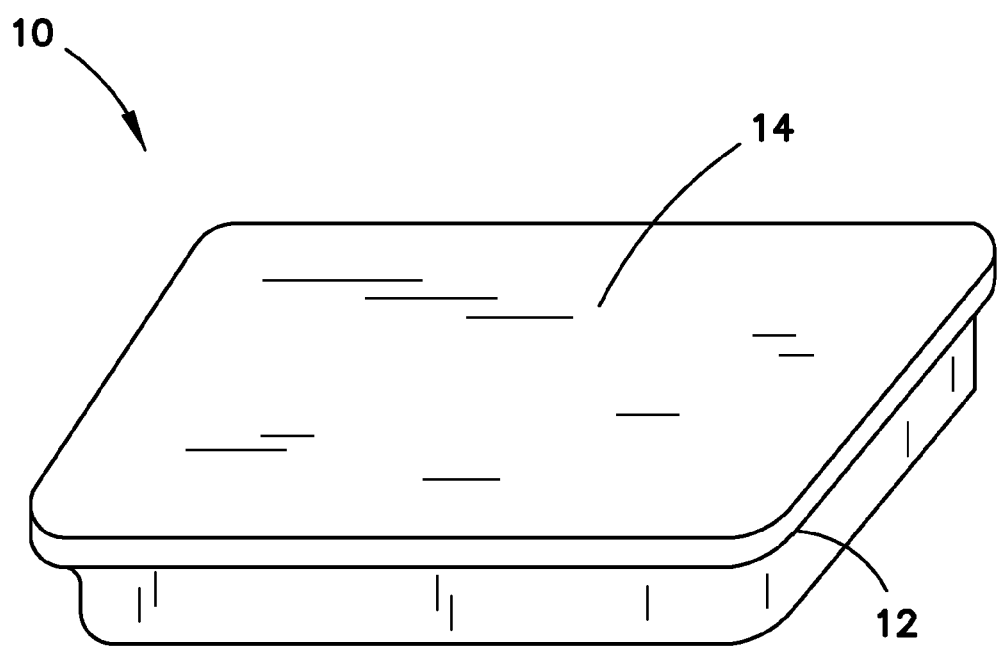
FIG. 1 is a perspective view of one example of a package.

For the purposes of promoting an understanding of the principles of the present disclosure, reference will now be made to the embodiments illustrated in the drawings, and specific language will be used to describe the same. Moreover, in the figures, like-referenced numerals designate corresponding parts throughout the different views.

FIG. 1 depicts a package 10 for storing and transporting medical devices and/or other contents that are to be maintained in a sterile environment before use. The package 10 can be configured specifically for moisture-sensitive medical devices, such as drug coated medical devices. The package 10 can include a bottom portion 12 and a top portion 14. The bottom portion 12 may be further contoured and shaped to retain the medical device in order to prevent relative movement of the device. Additional attachment features may also be used to further to prevent movement of the medical device within the package. One exemplary drug coated device is the SPECTRUM® Turbo-JeCT™ PICC (peripherally inserted central catheter) having a drug coating beneficial in inhibiting the blood infections, including at least one of minocycline and rifampin, or a combination thereof. The exemplary PICC is available at Cook Medical (Bloomington, Ind.). As can be appreciated by those skilled in the art, there are numerous other drug coated devices that can benefit from the packaging described herein. The packages described herein can extend the shelf life of drug coated medical devices from 1 year to about two years.

Figure 2:
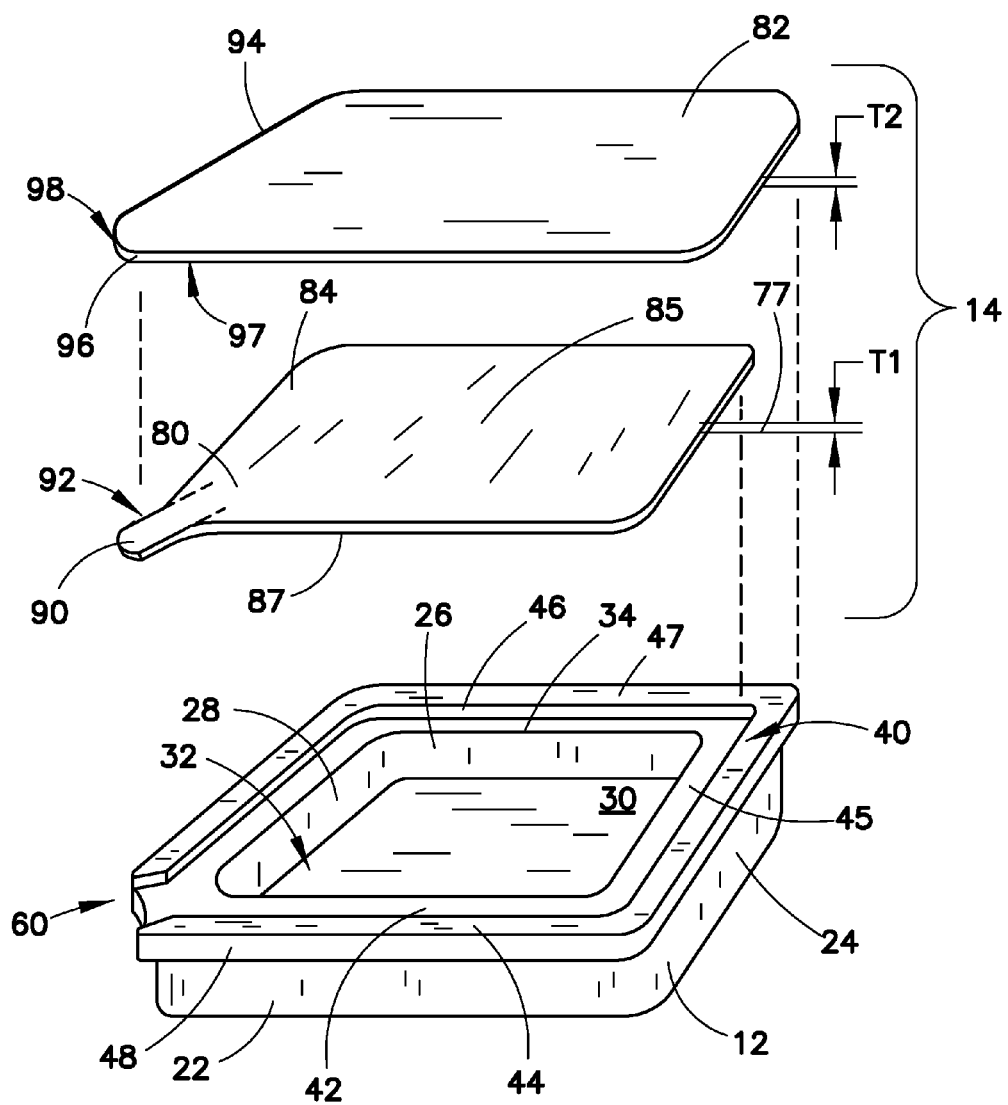
FIG. 2 is a perspective exploded view of a first example of the package of FIG. 1.

FIGS. 2-8 depict one example of the package 10. In FIG. 2, the bottom portion 12 can have sidewalls 22, 24, 26, 28, which together with a bottom wall 30 form a cavity 32 for receiving one or more medical devices (not shown). The bottom portion 12 can have a boxed shape, or can have any other shape known in the art that is used for similarly situated trays. As will be explained below, the top portion 14 can include at least an inner lid portion 80 and an outer lid portion 82 that can be sealably attached to the bottom portion to form the package 10 for containing the medical device.

A flange 40 can be formed along a top edge 34 of the sidewalls 22, 24, 26, 28 of the bottom portion 12. The flange 40 can extend outwardly away from the cavity 32. The flange 40 may include an inner recessed flange portion 42 and an outer flange portion 44 disposed outside the inner flange portion. The inner recessed flange portion can form first top surfaces 45 that are substantially coplanar with one another. The outer flange portion can form second top surfaces 47 that are substantially coplanar with one another.

Figure 3:
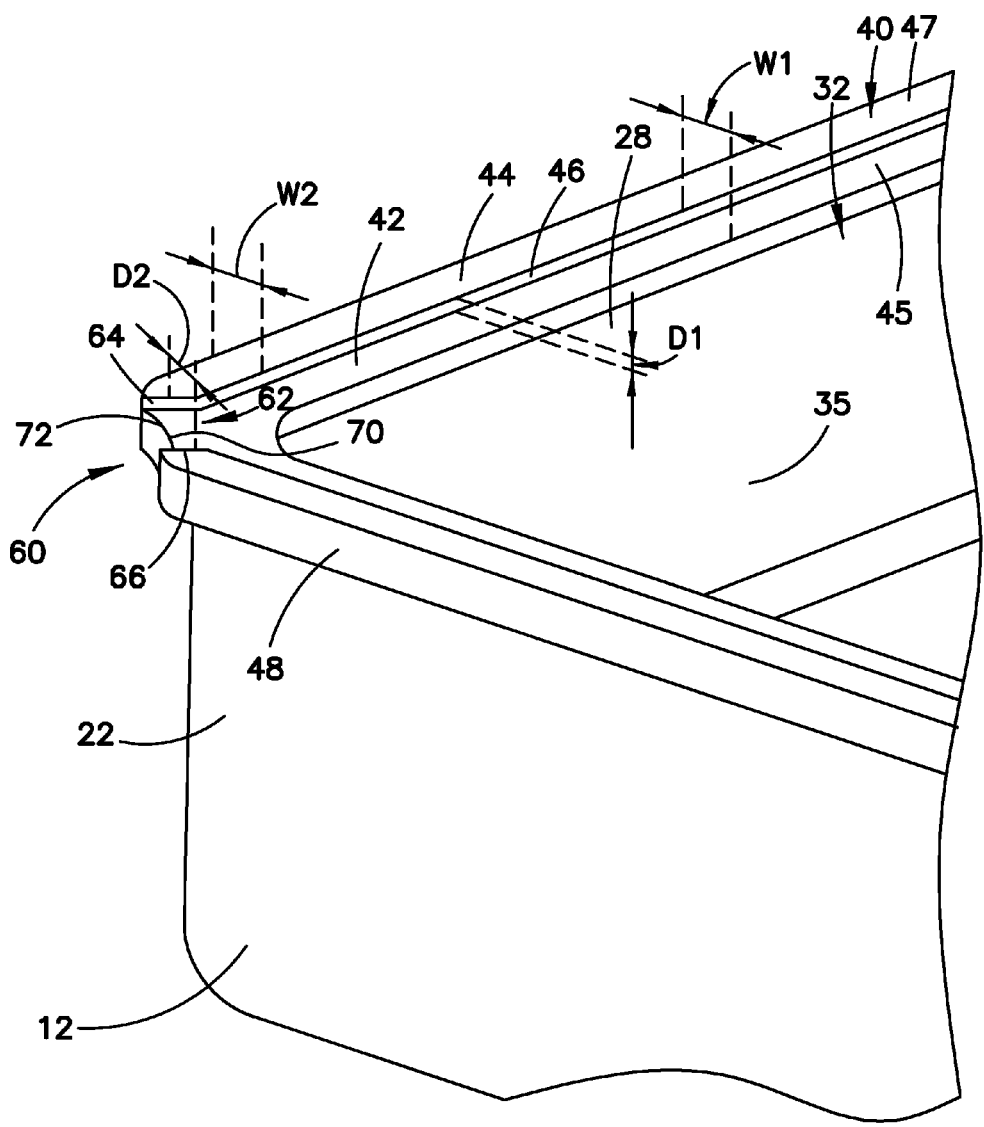
FIGS. 3-6 are perspective partial views of a method of making the first example of the package of FIG. 2.

In FIGS. 2-3, the inner recessed flange portion 42 can extend outward from an inner wall 35 of the cavity 32 to an inner flange wall 46 defined by the outer flange portion 44 that is elevated relative to the inner recessed flanged portion 42 by a distance D1. The distance of the outward extension of the inner recessed flange portion 42 can be at a width W1. The outer flange portion 44 can extend outward from the inner flange wall 46 to an outer flange periphery 48 of the flange 40. The distance of the outward extension of the outer flange portion 44 can be at a width W2.

At least one corner 60 of the bottom portion 12 can include a discontinuous portion 62 of the outer flange portion 44, thereby forming a channel. To this end, the outer flange portion 44 can have first and second ends 64, 66 that terminate at the corner 60 to form the walls of the channel. The walls of the channel can be extensions of the inner flange wall portion 46. The first and second ends 64, 66 can be separated from one another by a distance D2. At the corner 60, the inner recessed flange portion 42 is shown extending outward along the channel formed by the discontinuous portion 62 by a distance greater than W1. This arrangement can define a corner portion 70 of the outer flange periphery 48 of the flange 40. The general distance of the corner portion 70 may be the combination of widths W1 and W2. Alternatively, the distance may be slightly less than the combination of widths W1 and W2. An indentation 72 can be formed at the corner portion 70, relative to the adjacent portions of the outer flange periphery 48 of the flange 40.

The bottom portion 12 can be formed of any material known in the art that is suitable for storing and transporting medical devices. For example, the bottom portion can be formed of a translucent polymeric material, such as a transparent plastic, to permit viewing of a medical device disposed therein without opening the package. The material of the bottom portion may also be tinted with a light blue coloring or any other coloring. Optionally, the bottom portion may be formed of an opaque material, such as an opaque plastic, to inhibit the medical device from exposure to UV light, which may adversely affect the medical device (e.g. by activating or drying out prematurely an adhesive coating). The bottom portion may also be made from moisture-resistant materials. In addition, the bottom portion may further include release agents and other coatings such as silicone. Exemplary polymeric materials from which the bottom portion may be formed include, but are not limited to, polyethylene terephthalate (PET), polyethylene teraphtalate glycol (PETG), high-density polyethylene (HDPE), low-density polyethylene (LDPE), polyvinyl chloride (PVC), polypropylene (PP), polystyrene (PS), high impact polystyrene (HIPS), polycarbonate (PC), acrylonitrile butadiene styrene (ABS), and other appropriate polymeric materials, as will be appreciated by one of skill in the art. The bottom portion can be formed unitarily from a polymeric material by an injection molding process or thermoformed with a thermoformable material. However, it should be understood that the particular type of material and method of manufacture are not critical to the present invention. Trays in the form of the bottom portions can be commercially available from the Prent Corporation (Janesville, Wis.).

Other features can improve the strength or handling of the bottom portion 12. For example, the bottom portion may include depressions or raised portions that are configured to increase the strength thereof and/or prevent planar surfaces of the bottom portion from excessive bending or flexing. Similarly, the bottom portion 12 may have roughened surfaces to improve the tactile handling of the package.

Figure 4:
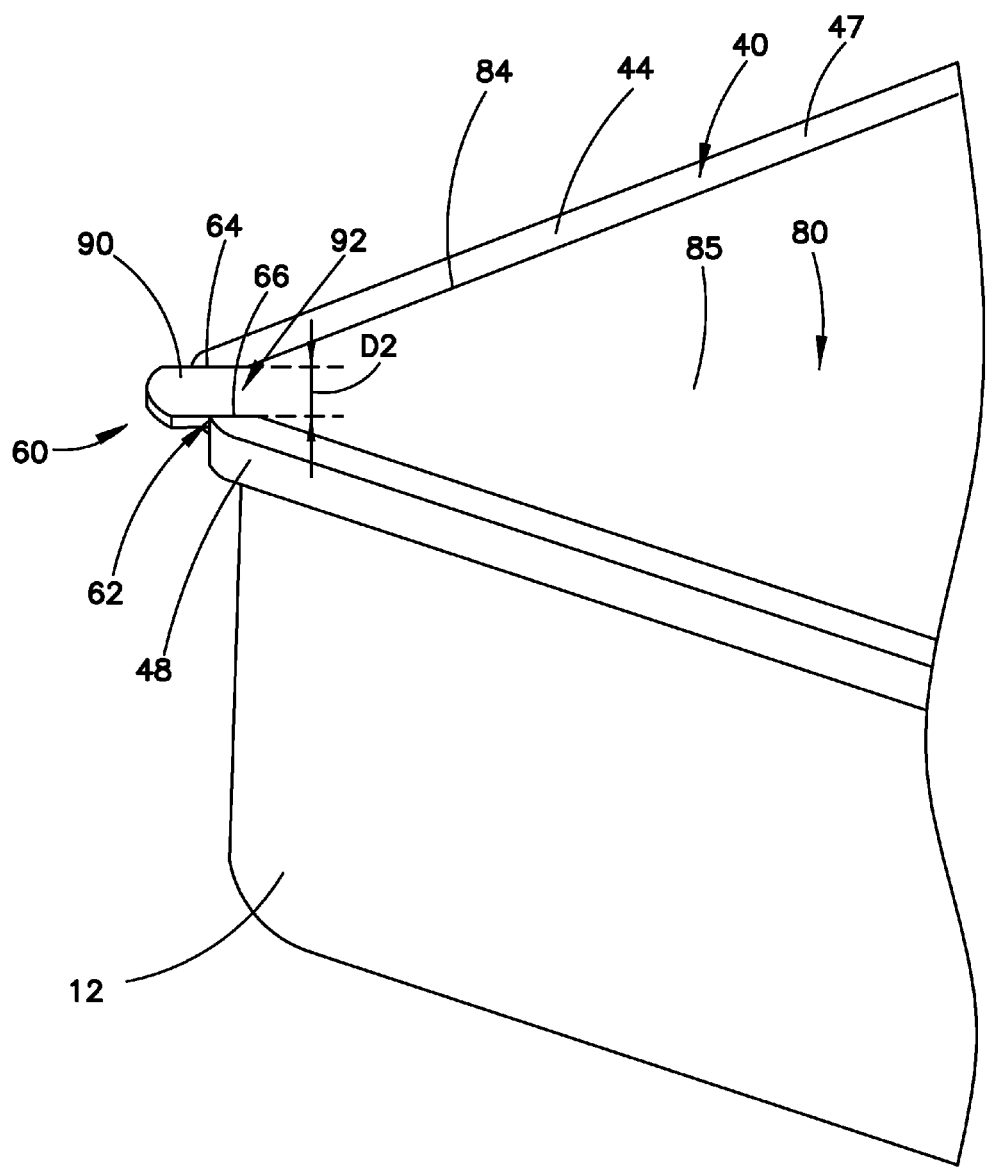

According to FIG. 2, the top portion 14 can include the inner lid portion 80 and the outer lid portion 82. The inner lid portion 80 can be a sheet of at least one material having an overall thickness T1 and an outer first periphery 84. The outer first periphery 84 is shaped and sized to be sealably attached to the first top surface 45 of the inner recessed flange portion 42 of the bottom portion 12, as shown in FIG. 4. For example, the outer first periphery 84 can be sized and shaped to be substantially identical to the shape and the size defined by the inner flange wall 46 so that portions of the inner lid portion 80 can engage, or at least be disposed proximate to, the inner flange wall 46. The thickness T1 of the inner lid portion 80 can be about the same distance as the recessed distance D1. To this end, when the inner lid portion 80 engages the first top surface 45 of the inner recessed flange portion 42, the upper surface 85 of the inner lid portion 80 can be substantially coplanar with the second top surface 47 of the outer flange portion 44, as shown in FIG. 4.

The inner lid portion 80 can also include a first tab 90 formed along at least one corner 92 of the inner lid portion 80. The first tab 90 can be sized and shaped to fit within the channel formed by the discontinuous portion 62 at the corner 60 of the bottom portion 12. For example, the first tab 90 can be an elongated body having a width that can be substantially the same as the separation distance D2 between the first and second ends 64, 66 of the outer flange portion. The length of elongated of the first tab 90 can extend beyond the indentation 72 of the outer flange periphery 48 of the flange 40 by a distance sufficient for an end user to grasp, such as up to about one inch.

The inner lid portion 80 can be made of a material configured to facilitate sterilization procedures. In one instance, the inner lid portion 80 can be a breathable material that is permeable to permit sterilizing gases such as steam, ethylene oxide, or Freon, and/or transparent to permit e-beams and gamma rays used in irradiative sterilization. The inner lid portion 80 may also constitute an impassible barrier to moisture, bacteria, viruses, and other substances that may compromise the sterility or are otherwise detrimental to the medical device and the packaging. One example of a material for the inner lid portion 80 having one or more of the properties is sold under the trademark TYVEK® (2FS, 1059B and 1073B), which is available from Medical Packaging Division of E.I DuPont de Nemours and Company (Wilmington, Del.). TYVEK® is a lightly consolidated or unconsolidated fabric made from spun HDPE, which can be also strong, puncture-resistant, and tear-resistant. Another example of a material for the inner lid portion 80 having one or more of the properties is commercially available as OVANTEX® of Oliver-Tolas Healthcare Packaging (Grand Rapids, Mich.). OVANTEX® is a blend of synthetic fibers and cellulose-based components. Other materials with at least one of the desired properties may be used for the inner lid portion.

Figure 7:
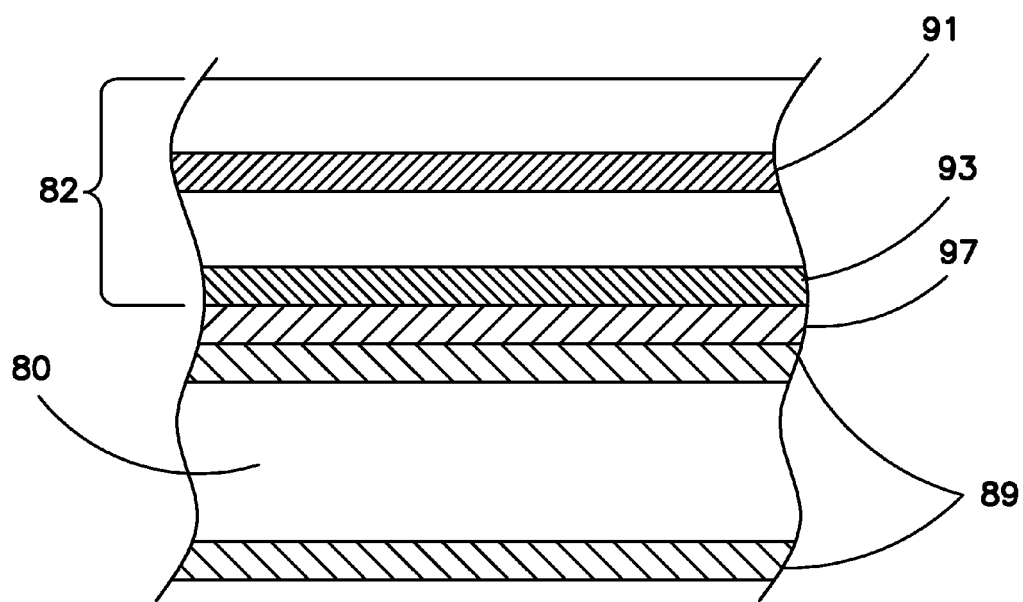
FIG. 7 is a cross-sectional view of one example of a top portion of the package of FIG. 1.

The inner lid portion 80 may be sealed to the first top surface 45 of the inner recessed flange portion 42 of the bottom portion 12 with an adhesive 89, as shown in FIG. 7. The adhesive 89 may be separately applied to the lid portion or the bottom portion before sealing. The adhesive 89 may be in the form of a coating that is applied to regions of the lower surface 87, the upper surface 85, the periphery, or any combination thereof, of the inner lid portion. In one example, the adhesive coating is applied to both of the lower and upper surfaces. The adhesive 89 may be applied to a pre-selected region, such as along the perimeter of the lower surface 87 of the inner lid portion 80 that is to confront and engage the corresponding the first top surface 45 of the inner recessed flange portion 42. The adhesive may be applied directly along the inner recessed flange portion 42 to limit adhesive exposure to the medical device. As a result, any adhesives in non-sealed areas, such as the central region of the inner lid portion 80 that is outlined by the perimeter, can be eliminated, thereby maximizing the porosity of the inner lid portion to shorten the sterilization cycles. One example of the adhesive is a hot melt heat-sealable adhesive, which can be in the form of a coating of the inner lid portion. The adhesive can be applied in a uniform dot pattern for high tack and peelable seal quality. The adhesive may have a blue tint that is activated during the heat-sealing process which can be interpreted as indicating the seal integrity. The adhesive can facilitate in maintaining the medical device enclosed within the cavity of the bottom portion in a moisture resistant and microbial contaminant resistant, sterile environment. Exemplary adhesives are commercially available as XHALE® hot melt adhesive with sure-seal DOTCOAT® technology or SEAL-SCIENCE® water based adhesive, both available from Oliver-Tolas.

Figure 5:
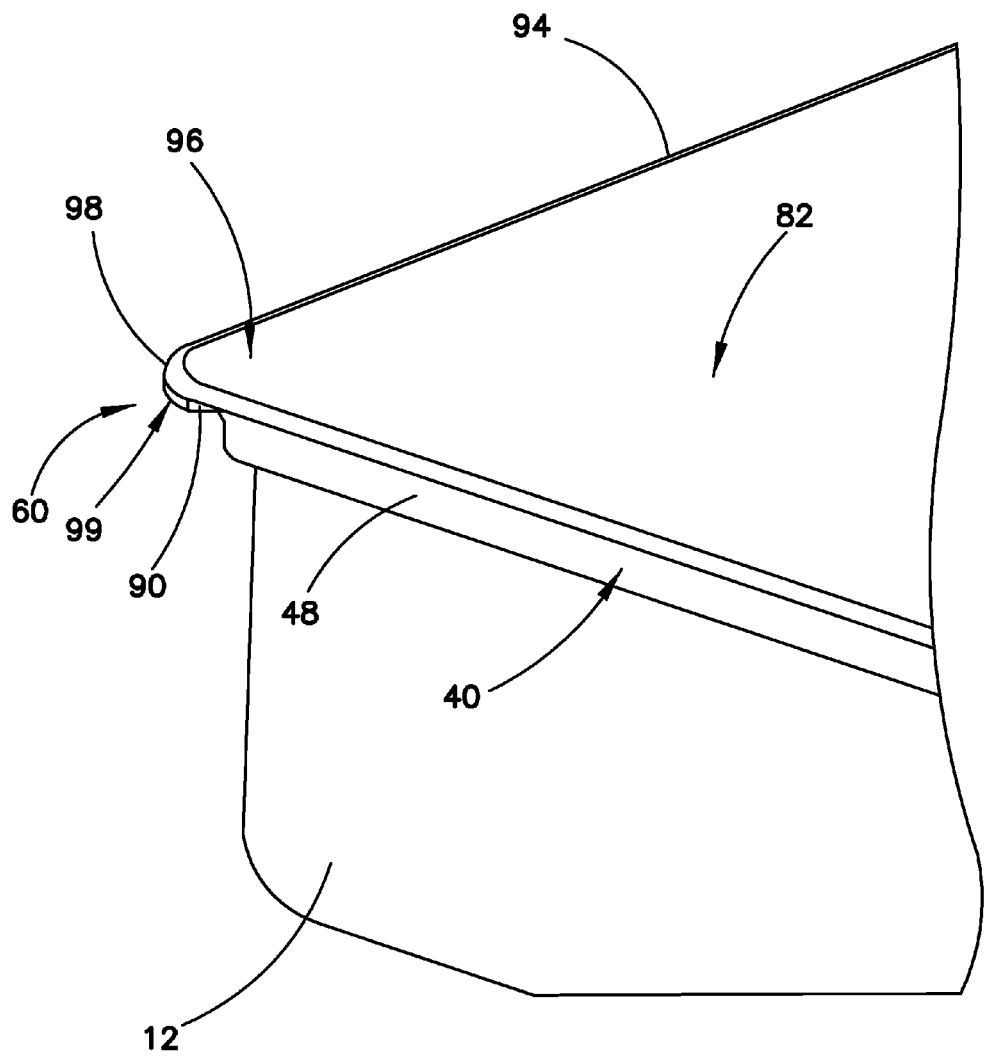

Referring back to FIG. 2, the outer lid portion 82 can be a sheet of at least one material having an overall thickness T2 and an outer second periphery 94. The outer second periphery 94 is shaped and sized to cover and overlie the inner lid portion 80 and to be sealably attached at least along the second top surface 47 of the outer flange portion 44 of the bottom portion 12, as shown in FIG. 5. For example, the outer second periphery 94 can be sized and shaped to be substantially identical to the shape and the size defined by the outer flange periphery 48. Portions of the outer lid portion 82 may also be sealably attached to the inner lid portion 80. For example, portions of the outer lid portion 82 can be sealably attached to at least portions of the inner lid portion 80 that correspond to the inner recessed flange portion 42. It is contemplated that the outer lid portion 82 can be attached to the other portions, in addition to or in place of such corresponding portions, of the inner lid portion 80.

Figure 6:
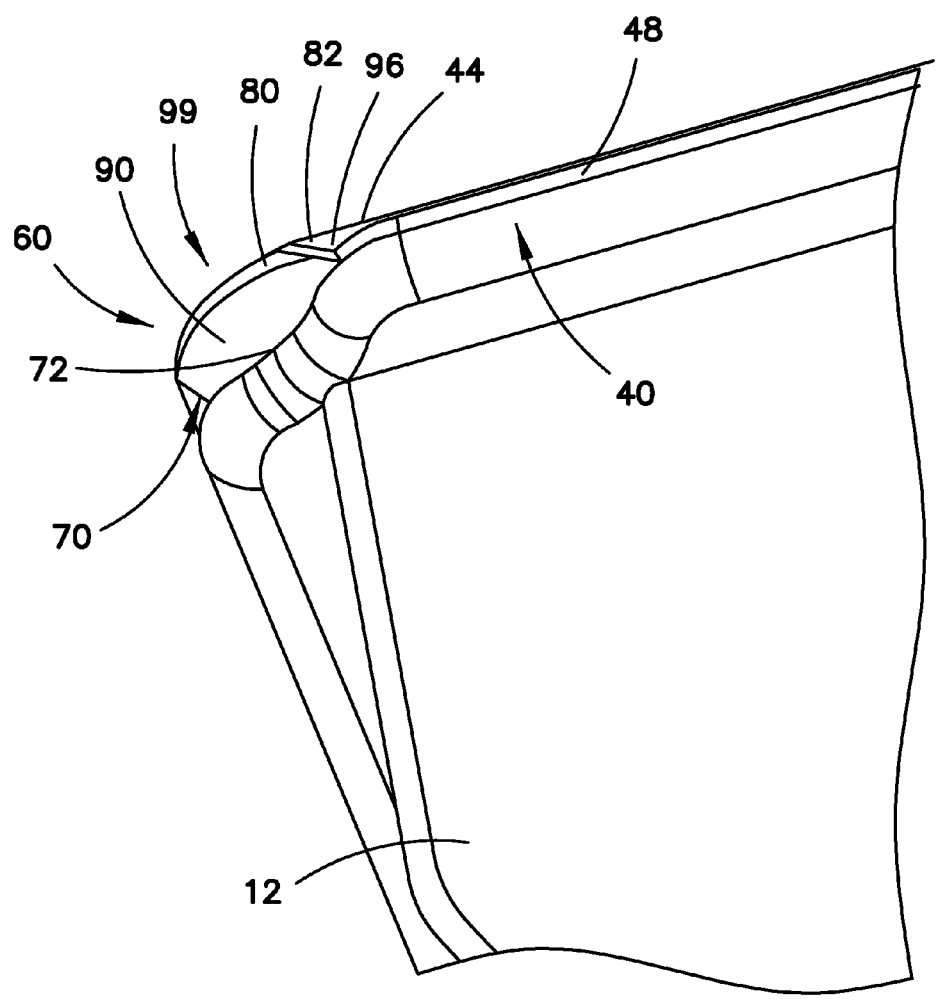

The outer lid portion 82 can include a second tab 96 formed along at least one corner 98 of the outer lid portion 82. The second tab 96 can be sized and shaped to fit over at least a portion of the first tab 90 of the inner lid portion. FIG. 6 depicts one example of the relative orientation of the first and second tabs 90, 96. The first and second tabs 90, 96 can extend past the indentation 72 of the corner portion 70 of the outer flange portion 44. The indentation 72 is sized to increase the grasping area of the tabs. As shown, portions of the second tab 96 may remain uncovered by the first tab. The outer extent of the first and second tabs can be similarly shaped, such as rounded. FIG. 5 shows one configuration of the second tab 96 having a shape that is substantially identical to the shape and size of the other corners of the outer lid portion so that the outer lid has uniform corners such as shown in FIG. 1.

The outer lid portion 82 can be made of a material configured to facilitate resistance to moisture. In one instance, the outer lid portion 82 can limit transmission of light, UV, vapor, and/or oxygen therethrough. The outer lid portion 82 can have multiple layers, such as shown in FIG. 7. At least one of the layers may include a metal foil layer 91, such as aluminum foil. In this embodiment, the metal foil layer 91 in addition to providing moisture and gas barrier properties can also provide UV barrier properties.

Another layer may be an environmental member, such as an environmental film 93, that is configured to limit the influence of ambient conditions (such as, e.g., light, moisture, and/or oxygen) which could affect the stability of the drug coated medical device and/or adhesives. It is contemplated that an environmental packet with similar functionality can be integrated between the outer and inner lid portions. The environmental film 93 or packet may include one or more of moisture desiccants, oxygen scavengers, carbon dioxide scavengers, and the like. Typical moisture desiccants may include silica gel, molecular sieves, calcium chloride, and the like. The environmental film can be selected for an intended purpose to regulate the cavity environmental conditions. For example, the environmental film may be particularly useful when portions of the inner lid portion, e.g., the first tab, are exposed to the ambient conditions after sealing of the outer lid portion. The environmental film may be attached at least one of the inner lid and/or the outer lid portions after sealing. It can be appreciated that the outer lid portion can include other layers to improve sealing, structural integrity, as well as other properties. Such layers can include PET, LDPE, a polyamide (nylon) layer, LDPE/ethylene vinyl acetate (EVA) layer for sealability.

In one example, the outer lid portion 82 comprises a multi-laminate structure that includes the metal foil layer 91 and the environmental layer 93. One such exemplary outer lid portion is commercially available as DM-5836 DesiVent™ provided by Alcan Packaging—Medical Flexibles Americas (Chicago, Ill.), having a minimum desiccant capacity of 3.4 pounds/ream. Here, the exemplary outer lid portion can include the following layers, typically in the following order: a 48 ga.

PET outermost layer, a 10-pound LDPE layer, a 35 ga. Aluminum foil, a 10-pound LDPE layer, and a 250 ga. peelable desiccant innermost film.

The outer lid portion 82 may be sealed to the second top surface 47 of the outer flange portion 44 of the bottom portion 12 with an adhesive 97 such as an adhesive material described above with respect to the adhesive 89. For example, the adhesive 97 may be separately applied to the lid portion or the bottom portion before sealing. The adhesive 97 may be in the form of a coating that is applied to regions of the lower surface, the periphery, or any combination thereof, of the outer lid portion. The adhesive 97 may be applied to preselected region, such as along the perimeter of the lower surface of the outer lid portion 82 that is to confront and engage the corresponding the second top surface 47 of the outer flange portion 44. The adhesive may be applied directly along the outer flange portion 44 to limit adhesive exposure to the medical device. Further, the first tab 90 may also be sealed to the second tab 96 and/or the outer lid portion with an adhesive to form a combined tab feature 99, although the tabs can be independently used. The combined tab 99 can facilitate peeling of both lid portions simultaneously.

FIG. 7 illustrates a partial cross-sectional view of one example of the inner and outer lid portions 80, 82. The inner lid portion 80 is coated on the upper and lower surfaces 85, 87 with the adhesive 89. The outer lid portion 82 can include the metal foil layer 91 and the environmental layer 93 positioned underneath the foil layer. The environmental layer can form the innermost layer of the outer lid portion, and can be coated with the adhesive 97 along the lower surface.

To open the first example of the package 10 to gain access to the contents therein, a hand of an end user can grasp the first and second tabs 90, 96, which preferably form the single combined tab feature 99. The end user can then apply a force to the first and second tabs 90, 96 in the direction upward away from the cavity and/or toward the corner opposite the tabs. The force is sufficient to break the seal formed by the adhesives 89, 97 at least along the second top surface 47 of the outer flange portion 44 and along the first top surface 45 of the inner recessed flange portion 42.

To make the first example of the package 10, a PETG thermoformed tray is formed to define the bottom portion. The PETG tray can have general dimensions of about 8"W× 12"L×1.5"D. The flange can be about 0.5 to 1 inches wide. In one example, the flange width is about 0.75 inches, with W1 measuring about 0.375 inches wide and W2 measuring about 0.375 inches wide, although the respective widths can be different sizes from one another. The inner recessed inner flange is recessed by a distance D1, which is about the thickness T1 of the inner lid portion, or about 0.75 mm to about 0.1 mm. One or more medical devices can be inserted into the tray, and preferably attached within the tray to prevent any relative movement therebetween.

The inner lid portion is a TYVEK® 10738 lidstock entirely coated with a heat-sealable adhesive material, having general dimensions of about 7.25"W×11.25"L×0.1 mm thickness for a 0.375-inch inner flange width. The inner lid portion is placed on the top surface of the inner recessed flange portion, with the first tab positioned at the desired corner. A first heat sealer with a die shaped for the intended shape of the first sealed region, i.e., the first top surface of the inner recessed flange or 0.375-inch width ring shape having an outer periphery sized about 7.25"W×11.25"L. The first heat sealer applies a pressure against the inner lid portion and the inner recessed flange portion for a predetermined temperature and time. The pressure, time, and temperature are selected to be sufficient to melt and bond the corresponding coating portions of inner lid portion to the top surface of the inner recessed flange portion of the PETG tray to form an enclosure for the medical device as an intermediate product.

After the first seal, sterilization can be applied by various means known in the art. For example, the package with the inner lid portion be exposed to sterilizing gases such as steam, ethylene oxide (ETO), or Freon, and/or radiation such as e-beams and gamma rays used in irradiative sterilization. After sterilization, the inner lid and the tray can form a microbial-resistant, sterile enclosure for the medical device. Since the inner lid portion is configured for preventing the passage of bacteria, the medical device or contents of the package will remain sterile until the seal formed by the inner lid portion is broken.

To enhance the moisture resistance of the microbial-resistant, sterile enclosure, the outer lid portion is placed on the top surface of the outer flange portion to overlie the sealed inner lid portion. The outer lid portion is a DM-5836 DesiVent™ moisture scavenging foil lamination that has at least the perimeter of the lower surface entirely coated with a heat-sealable adhesive material, having general dimensions of about 8"W×12"L×0.1 mm thickness for a 0.375-inch outer flange width. The outer lid portion is placed on the top surface, with the second tab positioned at the desired corner. A second heat sealer with a die shaped for the intended shape of the second sealed region, i.e., the second top surface of the outer flange portion or 0.375-inch width ring shape having an outer periphery sized about 8"W×12"L. The width of the ring of the second sealer may be greater toward the inner cavity so that portions of the outer lid portion can also seal to the inner lid portion. The second heat sealer applies a pressure against the outer lid portion and the outer flange portion for a predetermined temperature and time. The pressure, time, and temperature are selected to be sufficient to melt and bond the corresponding coating portions of outer lid portion to the top surface of the outer flange portion of the PETG tray to form a final product of a moisture-resistant, microbial-resistant, sterile enclosure for the medical device. Portions of the first and second tabs and portions of the outer lid portion inward of the outer flange portion may also be bonded to form the combined tab.

FIGS. 8-13 depict another example of the package 10. Identical names for features will be used in the description of this second example to designate substantially identical features described in the first example of the package. Thus, for the sake of brevity, it can be appreciated by those skilled in the art that some of the features described only with the first example of the package can be incorporated with the second example of the package.

Figure 8:
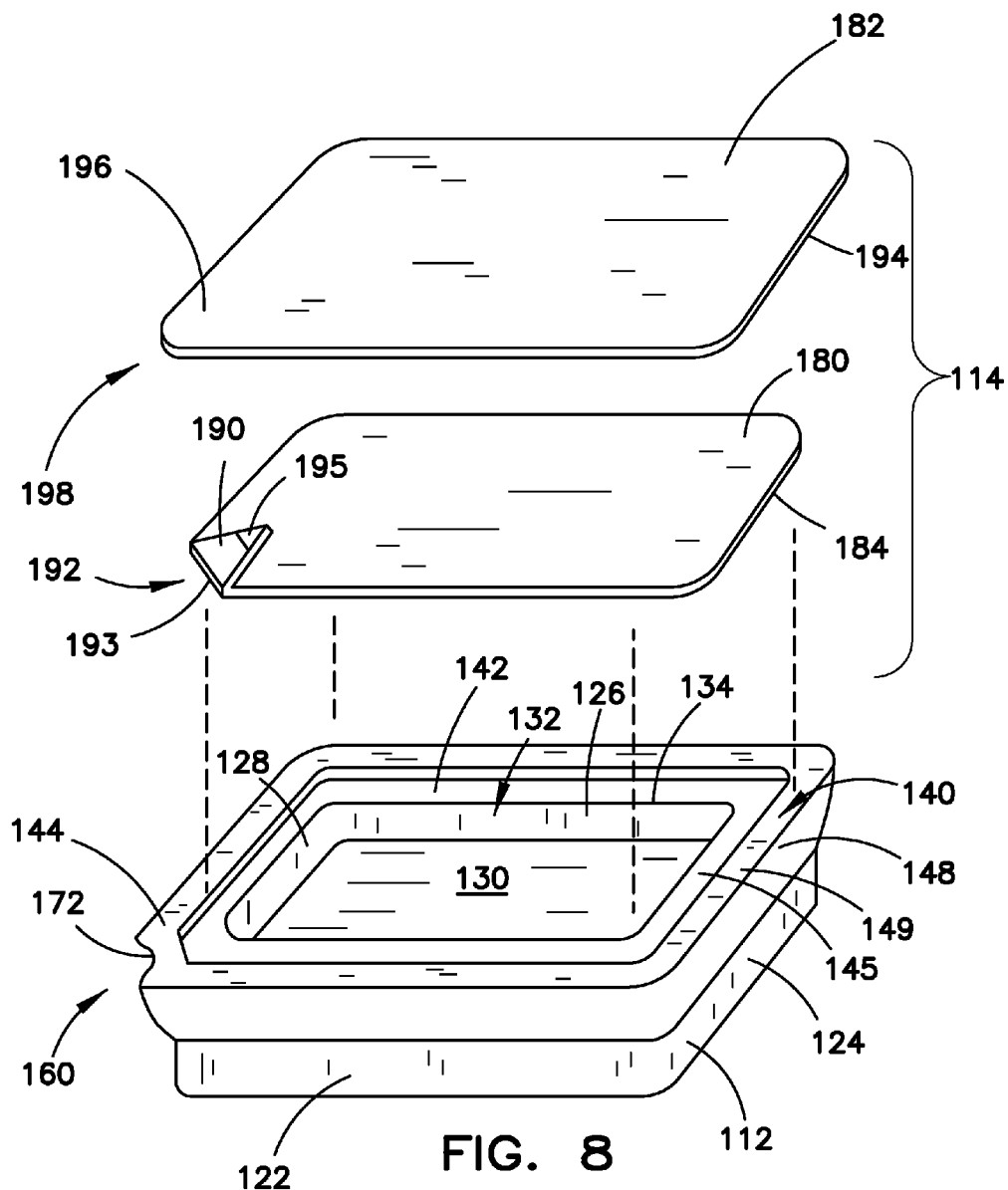
FIG. 8 is a perspective exploded view of a second example of the package of FIG. 1.

In FIG. 8, the bottom portion 112 having features similar to the bottom portion 12 of the first embodiment, can have sidewalls 122, 124, 126, 128, which together with the bottom wall 130 form the cavity 132 for receiving a medical device (not shown). The flange 140 can be formed along the top edge 134 of the sidewalls 122, 124, 126, 128 of the bottom portion 112. The flange 140 can extend outward away from the cavity 132. The flange 140 may include the inner recessed flange portion 142 and the outer flange portion 144.

Figure 9:
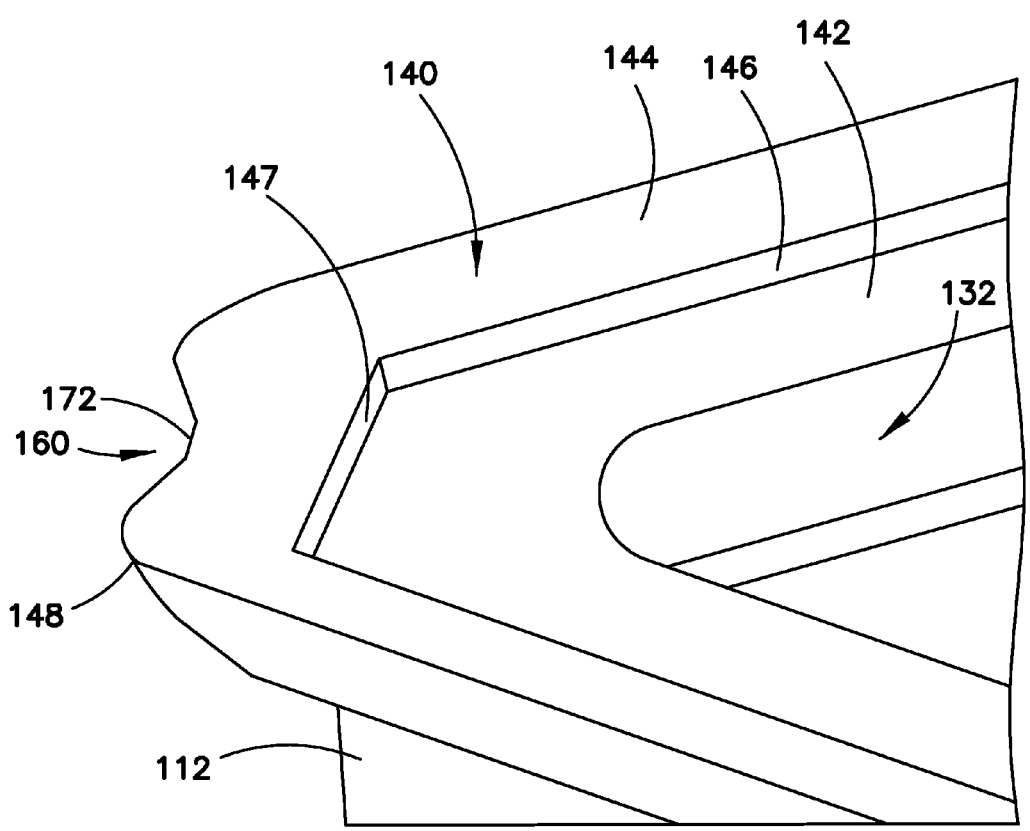
FIGS. 9-12 are perspective partial views of a method of making the second example of the package of FIG. 8.
Figure 10:
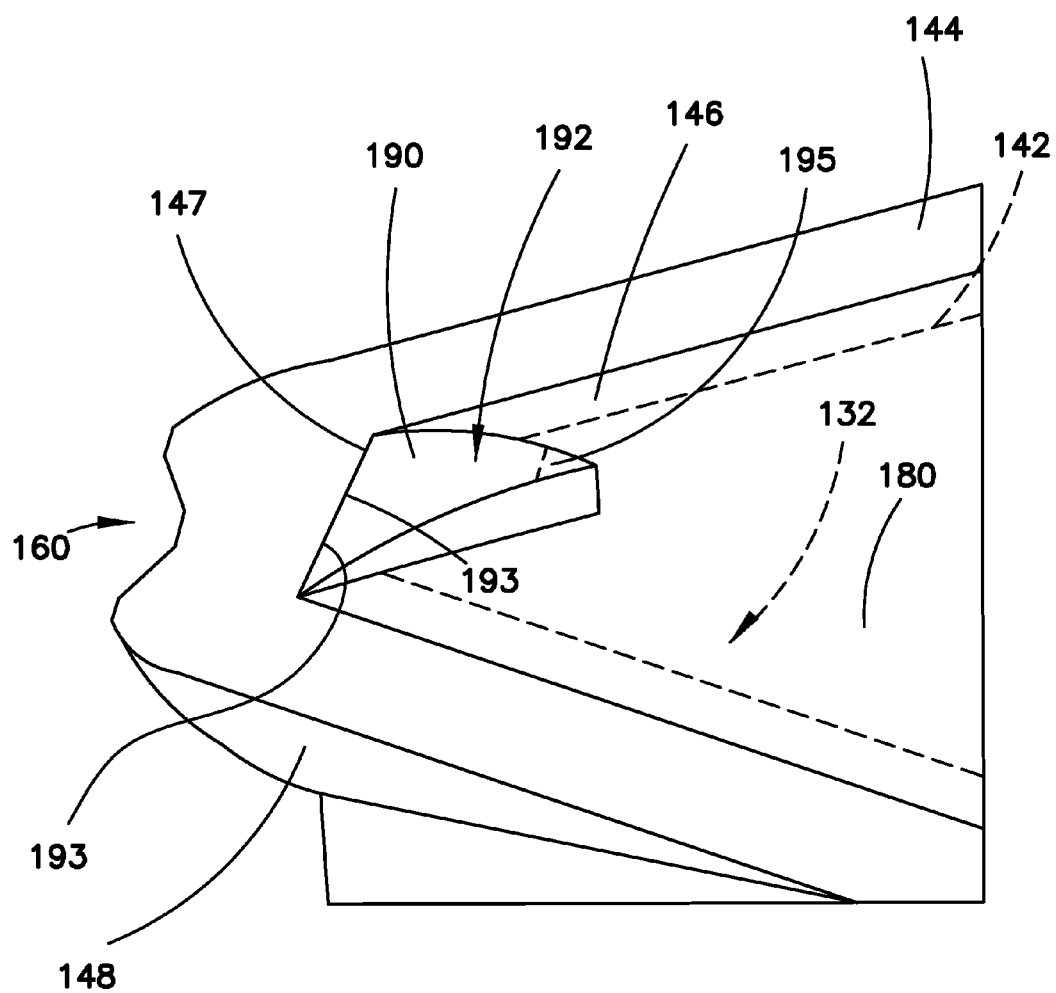

In FIGS. 9-10, the inner recessed flanged portion 142 can extend outward from the inner wall of the cavity 132 to the inner flange wall 146 defined by the outer flange portion 144 that is elevated relative to the inner recessed flanged portion 142. At least one corner 160 of the bottom portion 112 along the outer flange portion 144 includes the indentation 172 formed in the outer flange periphery 148 of the flange 140. The connection of respective portions of the inner flange wall 146 at the corner 160 may be by an intersecting wall portion 147 to define a closed ended corner. The intersecting wall portion 147 can be planar and obliquely oriented with respect to the respective connecting portions of the inner flange wall 146.

According to FIG. 8, the top portion 114 can include the inner lid portion 180 and the outer lid portion 182, each having features similar to the inner and outer lid portions of the first example. The outer first periphery 184 of the inner lid portion 180 is shaped and sized to be sealably attached to the first top surface 145 of the inner recessed flange portion 142 of the bottom portion 112, as shown in FIG. 10. For example, the outer first periphery 184 can be sized and shaped to be substantially identical to the shape and the size defined by the inner flange wall 146. This feature permits portions of the inner lid portion 180 to engage, or at least be disposed proximate to, the inner flange wall 146. The inner lid portion 180 can also include the first tab 190 formed along at least one corner 192 of the inner lid portion 180. The first tab 190 can be folded about a fold line toward the cavity 132, and in one example can take a triangular shape. When folded, a portion 193 of the inner lid portion 180 defined by the fold line, i.e., the base of the triangular shape, can be sized to engage the intersecting wall portion 147. A segment 195 of the first tab 190, e.g., the outer surface of the tip of the triangular shape, can be disposed across the cavity of the bottom portion to engage with the outer lid portion.

Figure 11:
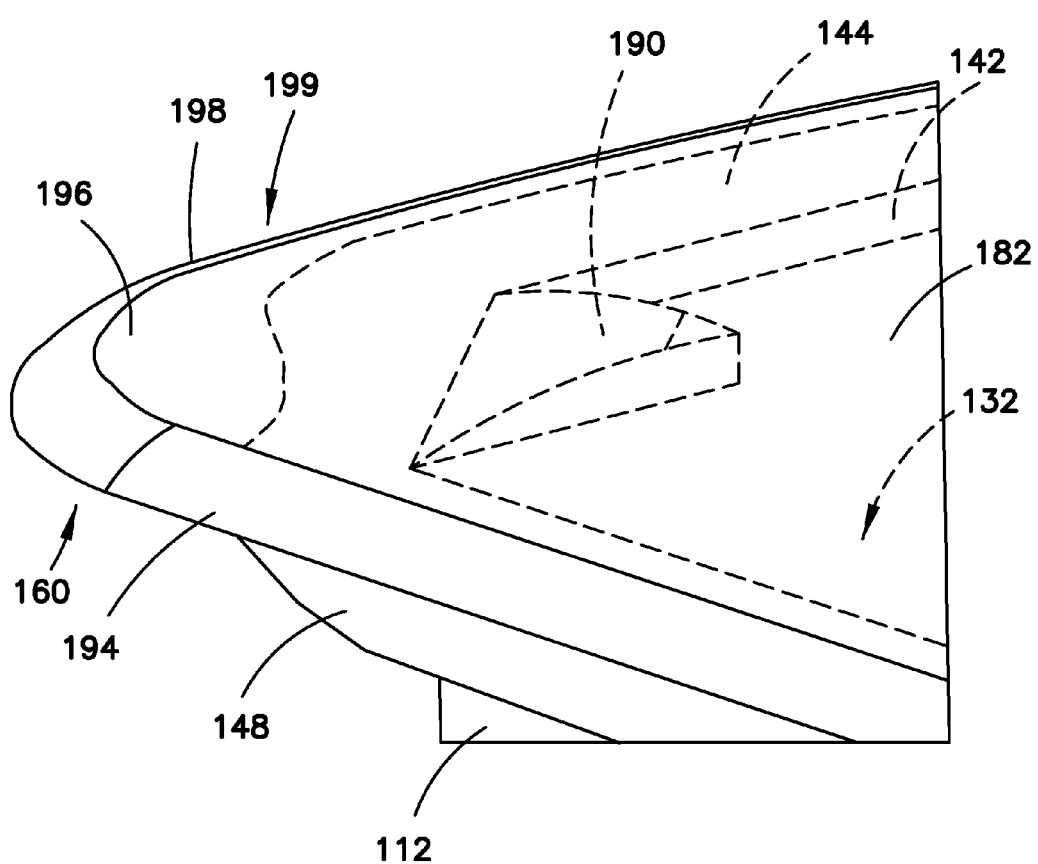

The outer second periphery 194 of the outer lid portion 182 is shaped and sized to overlie and cover the inner lid portion 180 and to be sealably attached at least to the second top surface 149 of the outer flange portion 144 of the bottom portion 112, as shown in FIG. 11. For example, the outer second periphery 194 can be sized and shaped to be substantially identical to the shape and the size defined by the outer flange periphery 148. Portions of the outer lid portion 182 may also be attached to the inner lid portion 180. For example, portions of the outer lid portion 182 can be attached to at least portions of the inner lid portion 180 that correspond to the inner recessed flange portion 142. It is contemplated that the outer lid portion 182 can be attached to the other portions, in addition to or in place of such corresponding portions, of the inner lid portion 180. The outer lid portion 180 can be attached to the respective components when the first tab 192 is folded inward. For example, the first tab, such as tip portion 195, may have an adhesive applied thereto for bonding to the lower surface of the outer lid portion 182. However, when the inner lid portion is coated with an adhesive on the upper and lower surfaces, the first tab can be capable of bonding without having an additional adhesive.

Figure 12:
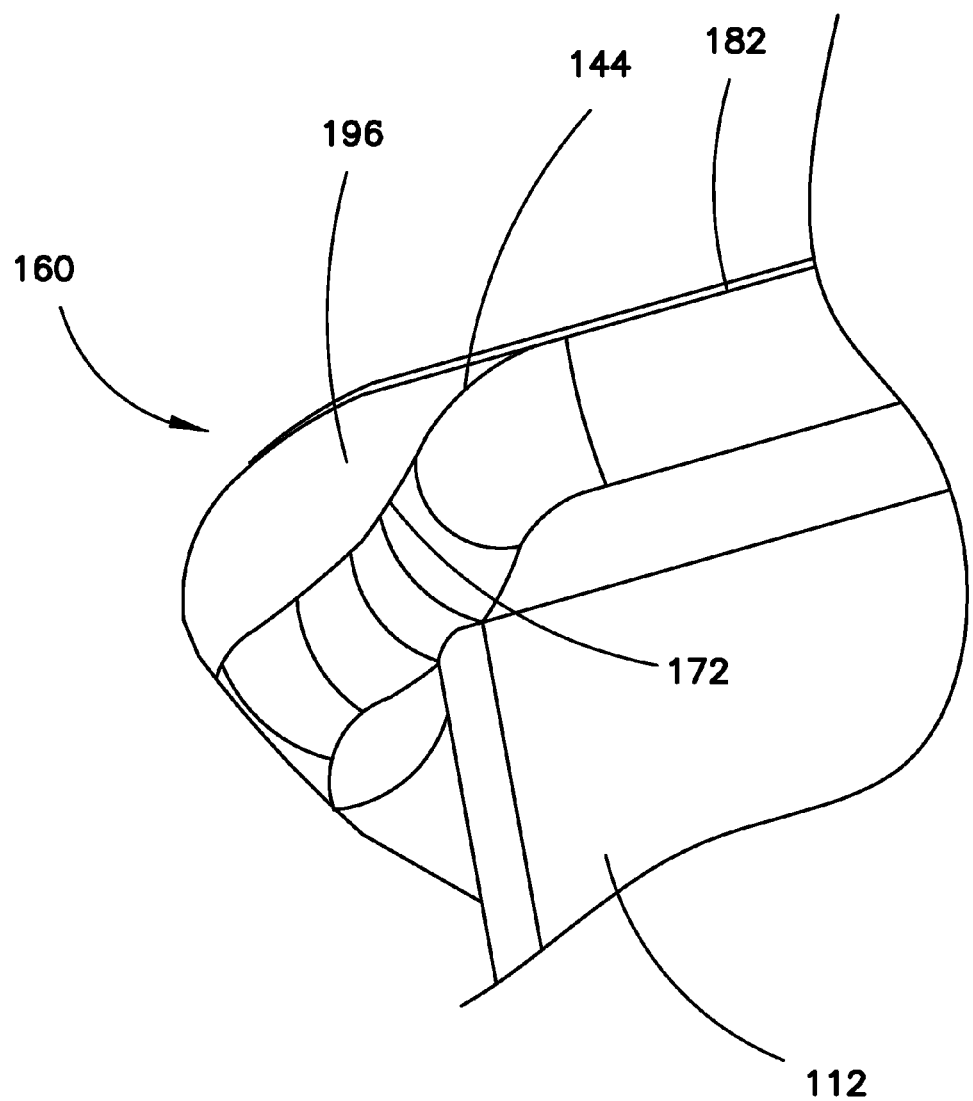

In FIG. 11, the outer lid portion 182 can also include the second tab 196 formed along at least one corner 198 of the outer lid portion 182. The second tab 196 can be sized and shaped to extend past the indentation 172. FIG. 12 depicts one example of the relative orientation of the second tab 196 at the corner 160. The second tab 196 can extend past the indentation 172 of the outer flange portion 144 in order to increase the grasping area of the second tab 196. When the portion 195 of the first tab 190 of the inner lid portion 180 is attached to the lower surface of the outer lid portion 182, a combined tab feature 199 can be formed.

To open the second example of the package 10 to gain access to the contents therein, a hand of an end user can grasp the second tab 96. The end user can then apply a force to the second tab 96 in the direction upward away from the cavity and/or toward the corner opposite the tabs. The force can be sufficient to break the seal of the adhesive along the second top surface 149 of the outer flange portion 144. Meanwhile, as the outer lid portion is continued to be pulled, the inner lid portion 180 can be pulled in the similar direction to break the seal of the adhesives along the inner flange portion. Preferably, the bonding of the folded first tab 190 to the lower surface of the outer lid portion 182 can permit a single pull to break the respective seals. After forming an access opening to the cavity of sufficient size with removal of the inner and outer lid portions, the end user can retrieve the medical device or contents from the package.

To make the second example of the package 10, the inner lid portion is sealed to the PETG tray above. The inner lid portion is a TYVEK® 1073B lidstock coated with a heat-sealable adhesive material, having general dimensions of about 7.25"W×11.25"L×0.1 mm thickness for a 0.375-inch inner flange width. The inner lid portion is placed on the top surface of the inner recessed flange portion, with the first tab positioned at the desired corner. The first heat sealer as described above applies a pressure against the inner lid portion and the inner recessed flange portion for a predetermined temperature and time to form the enclosure for the medical device as the intermediate product. At which time, sterilization can be applied by various means known in the art as described above to form the microbial-resistant, sterile enclosure for the medical device. The first tab can be folded about a fold line toward the cavity of the PETG tray, and thus can take the shape of a triangle. When folded, the base of the triangular shape can engage the inner wall flange.

The outer lid portion is a DM-5836 DesiVent™ moisture scavenging foil lamination, which at least has the perimeter of the lower surface entirely coated with a heat-sealable adhesive material, having general dimensions of about 8"W× 12"L×0.1 mm thickness for a 0.375-inch outer flange width. The outer lid portion is placed on the top surface of the outer flange portion, with the second tab positioned at the desired corner. The outer lid portion can capture the first tab in the folded configuration. The second heat sealer as described above applies a pressure against the outer lid portion and the outer flange portion for a predetermined temperature and time. The pressure, time, and temperature are selected to be sufficient to melt and bond the corresponding coating portions of outer lid portion to the top surface of the outer flange portion of the PETG tray to form a final product of a moisture-resistant, microbial-resistant, sterile enclosure for the medical device. A sufficient amount of heat may be conducted through the metal foil to cause the confronting coated portions of the outer lid portion and at least the tip of the first tab, which is the lower surface, to bond.

Figure 13:
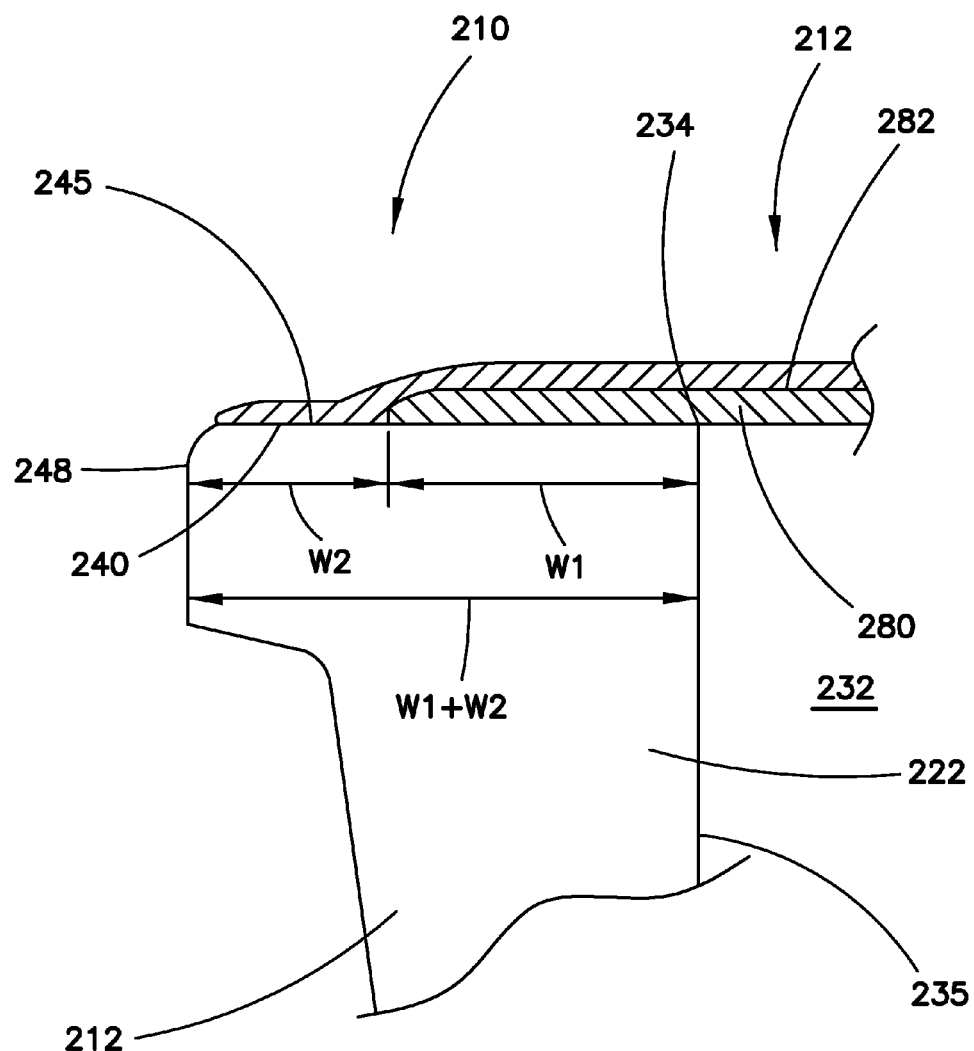
FIG. 13 is a cross-sectional view of a third example of the package of FIG. 1.

FIG. 13 illustrates a third example of the package, referenced now as a package 210, which incorporates at least one of the all of features of the package discussed previously. Identical names for features will be used in the description of this third example to designate substantially identical features described in the first and second examples of the package. Thus, for the sake of brevity, it can be appreciated by those skilled in the art that some of the features described only with the first and the second examples of the package are to be incorporated with the second example of the package.

In FIG. 13, the bottom portion 212 can have sidewalls, which together with the bottom wall form the cavity for receiving a medical device (not shown). The top portion 214 can include at least the inner lid portion 280 and the outer lid portion 282 that can be sealably attached to the bottom portion to form the package 210 for containing the medical device. The flange 240 can be formed along the top edge 234 of the sidewall 222. The flange 240 can extend outward away from the cavity 232. In this example, the flange 240 is a single level having top surfaces 245 that are substantially coplanar with one another. The flange 240 can extend outward from the inner wall 235 of the cavity 232 to the outer flange periphery 248 of the flange 240 by a distance of the summation of widths W1 and W2.

The inner lid portion 280 can be placed along and sealed to an inner portion of the flange 240, as defined by the width W1. The outer lid portion 282 can be placed along and sealed to an outer portion of the flange 240, as defined by the width W2. At least one corner of the package 210 can have the indentation. The lid portions can be configured to have either of the tab features described previously, such as shown in FIG. 5 or FIG. 11. Thus, to open the third example of the package 210 to gain access to the contents therein, a hand of an end user can grasp one or both tabs at the corner. The end user can then apply a force to the respective tabs in the direction upward away from the cavity and/or toward the corner opposite the tabs. The force can be sufficient to break the seal of the adhesive along the outer portion of the flange 240. Meanwhile, as the outer lid portion is continued to be pulled, the inner lid portion 180 can be pulled in the similar direction to break the seal of the adhesives along the inner portion of the flange 240. Preferably, the tabs are bonded to permit a single pull to break the respective seals. After forming an access opening to the cavity of sufficient size with removal of the inner and outer lid portions, the end user can retrieve the medical device or contents from the package.

Those skilled in the art will appreciate that all dimensions, compositions, etc., described herein are exemplary only, and that other appropriate dimensions, compositions, etc., may be substituted in an appropriate case. For example, the respective dimensions of the bottom portion and the inner and outer lid portions are exemplary, and may be varied based upon the intended use and/or performance of the package.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A package for containing a medical device, the package comprising:
   a bottom tray comprising sidewalls and a bottom wall to define a cavity to receive the medical device, a flange extending outward from top edges of the sidewalls, the flange comprising an inner flange portion and an outer flange portion disposed outside of the inner flange portion;
   an inner lid adhesively sealed to the inner flange portion at a first sealed region, the first sealed region forming a microbial-resistant, sterile seal between the inner lid and the inner flange portion, the inner lid comprising a sterilizable material that is permeable to a sterilizing gas to allow the medical device to be sterilized when the inner lid is sealed to the bottom tray, the inner lid and the bottom tray forming a microbial-resistant, sterile enclosure for the medical device; and
   an outer lid overlying the inner lid and adhesively sealed to the outer flange portion at a second sealed region, the second sealed region forming a microbial-resistant, sterile seal between the outer lid and the outer flange portion, the outer lid comprising a metal foil layer and an environmental member disposed between the metal foil layer and the inner lid,
   wherein a corner portion of the outer lid extends outward beyond a corner of the flange of the bottom tray, whereby, upon application of a withdrawing force to the corner portion of the outer lid, the inner lid and the outer lid are capable of being peeled together from the bottom tray.

2. The package of claim 1, wherein a corner portion of the inner lid comprises a first tab that is folded inward toward the cavity in a folded configuration and adhesively bonded to a lower surface of the outer lid.

3. The package of claim 2, wherein the inner flange portion and the outer flange portion are joined to one another by a flange wall extending around an entire periphery of the inner flange portion, the flange wall comprises an intersecting wall portion disposed at the corner of the flange and oriented obliquely relative to two adjacent connecting portions of the flange wall, and a fold line of the inner lid engages the intersecting wall portion of the flange wall.

4. The package of claim 1, wherein a corner portion of the inner lid comprises a protruding portion to form a first tab, and the corner portion of the outer lid overlies the first tab.

5. The package of claim 1, wherein at least one of the inner lid and the outer lid comprises a heat-sealable adhesive coating.

6. The package of claim 1, wherein each of the first sealed region and the second sealed region extends around an entire periphery of the cavity.

7. The package of claim 1, wherein the environmental member comprises a moisture desiccant.

8. The package of claim 7, wherein the moisture desiccant comprises at least one of silica gel, a molecular sieve, or calcium chloride.

9. The package of claim 1, wherein the environmental member comprises an environmental film, and the outer lid comprises a multi-laminate structure comprising the metal foil layer and the environmental film.

10. The package of claim 1, wherein the environmental member comprises an environmental packet disposed between the metal foil layer and the inner lid.

11. The package of claim 1, wherein the inner flange portion is recessed below the outer flange portion.

12. The package of claim 1, wherein the inner flange portion and the outer flange portion are coplanar with one another.

13. A package for containing a medical device, the package comprising:
   a bottom tray comprising sidewalls and a bottom wall to define a cavity to receive the medical device, a flange extending outward from top edges of the sidewalls, the flange comprising an inner flange portion and an outer flange portion disposed outside of the inner flange portion;
   an inner lid releasably sealed to the inner flange portion at a first sealed region, the first sealed region forming a microbial-resistant, sterile seal between the inner lid and the inner flange portion, the inner lid comprising a sterilizable material that is permeable to a sterilizing gas to allow the medical device to be sterilized when the inner lid is sealed to the bottom tray, the inner lid and the bottom tray forming a microbial-resistant, sterile enclosure for the medical device; and an outer lid overlying the inner lid and releasably sealed to the outer flange portion at a second sealed region, the second sealed region forming a microbial-resistant, sterile seal between the outer lid and the outer flange portion, the outer lid comprising a moisture barrier layer and an environmental member disposed between the moisture barrier layer and the inner lid.

14. The package of claim 13, wherein a corner portion of the outer lid extends outward beyond the flange of the bottom tray, whereby, upon application of a withdrawing force to the corner portion of the outer lid, the inner lid and the outer lid are capable of being peeled together from the bottom tray.

15. The package of claim 14, wherein a corner portion of the inner lid comprises a protruding portion extending outward beyond the flange of the bottom tray to form a first tab, and the corner portion of the outer lid overlies the first tab.

16. The package of claim 13, wherein the moisture barrier layer comprises a metal foil layer.

17. The package of claim 13, wherein a corner portion of the inner lid comprises a first tab that is folded inward toward the cavity in a folded configuration, and the first tab comprises a tip portion that is bonded to a lower surface of the outer lid.

18. The package of claim 13, wherein each of the inner flange portion and the outer flange portion extends around an entire periphery of the cavity.

19. The package of claim 13, wherein the environmental member comprises an environmental film, and the outer lid comprises a multi-laminate structure comprising the moisture barrier layer and the environmental film.

* * * * *